United States Patent
Chauhan et al.

(12)

(10) Patent No.: US 10,595,484 B2
(45) Date of Patent: Mar. 24, 2020

(54) **OMEGA-3 RICH HIGH YIELDING CULTIVAR OF *PERILLA FRUTESCENS* 'CAP HEMA'**

(71) Applicant: Centre for Aromatic Plants, Dehradun, Uttarakhand (IN)

(72) Inventors: Nirpendra Kumar Chauhan, Dehradun (IN); Syed Zafar Haider, Dehradun (IN); Ujjwal Bhandari, Dehradun (IN); Sher Singh, Dehradun (IN); Hema Lohani, Dehradun (IN); Sunil Sah, Dehradun (IN); Rakesh Kumar Yadav, Dehradun (IN); Dilawar Singh, Dehradun (IN); Garima Gwari, Dehradun (IN); Bhupendra Singh, Dehradun (IN)

(73) Assignee: CENTRE FOR AROMATIC PLANS, Dehradun (IN)

( * ) Notice: Subject to any disclaimer, the term of this patent is extended or adjusted under 35 U.S.C. 154(b) by 166 days.

(21) Appl. No.: 15/715,894

(22) Filed: Sep. 26, 2017

(65) Prior Publication Data
US 2019/0090448 A1    Mar. 28, 2019

(51) Int. Cl.
*A01H 5/10* (2018.01)
*A01H 6/50* (2018.01)
*A01H 5/12* (2018.01)

(52) U.S. Cl.
CPC ............... *A01H 5/10* (2013.01); *A01H 5/12* (2013.01); *A01H 6/50* (2018.05)

(58) Field of Classification Search
CPC ....................................................... A01H 6/50
See application file for complete search history.

(56) References Cited

PUBLICATIONS

Gwari et al Journal of Essential Oil Research 2016 vol. 28, No. 1, pp. 49-54 published online on Oct. 5, 2015 (Year: 2015).*
T. Longvah and Y.G. Deosthale, Chemical and Nutritional Studies on Hanshi (*Perilla frutescens*), a Traditional Oilseed from Northeast India, Journal of the American Oil Chemists' Society, Oct. 1991, pp. 781-784, vol. 68, No. 10.
T. Longvah and Y.G. Deosthale, Effect of Dehulling, Cooking and Roasting on the Protein Quality of *Perilla frutescens* Seed, Food Chemistry, 1998, pp. 519-523, vol. 63, No. 4, Elsevier Science Ltd., Great Britain.
P.G. Peiretti, Fatty Acid Content and Chemical Composition of Vegetative Parts of *Perilla* (*Perilla frutescens* L.) after Different Growth Lengths, Research Journal of Medicinal Plant, 2011, pp. 72-78, Academic Journals Inc.
Hyo-Sun Shin and Sung-Whan Kim, Lipid Composition of *Perilla* Seed, Journal of the American Oil Chemists' Society, Jun. 1994, pp. 619-620, vol. 71 No. 6, AOCS Press.

* cited by examiner

*Primary Examiner* — David H Kruse
(74) *Attorney, Agent, or Firm* — Workman Nydegger

(57) ABSTRACT

The present invention relates to a novel and distinct cultivar of *Perilla frutescens* designated as 'CAP HEMA' The new cultivar is rich in omega-3 and having high seed and fatty oil yield. A method for producing new cultivar of *Perilla frutescens* plant which comprises selection of half-sib family from wild type populations. The method further comprises evaluation for the yield attributing characters of selected strains in field conditions. The genotype produced is distinct, uniform and stably maintained by continuous rouging of off types in the population at early seedling stage from nursery itself and suitable for commercial cultivation.

8 Claims, 5 Drawing Sheets
Specification includes a Sequence Listing.

FIG. 1 shows the plant of *Perilla frutescens* cultivar 'CAP HEMA';

FIG. 2(a-d) DNA profile of the plant CAP HEMA (M is the size standard. Lanes 1-3 are control samples whereas lane 4 is the provided sample of the plant CAP HEMA)

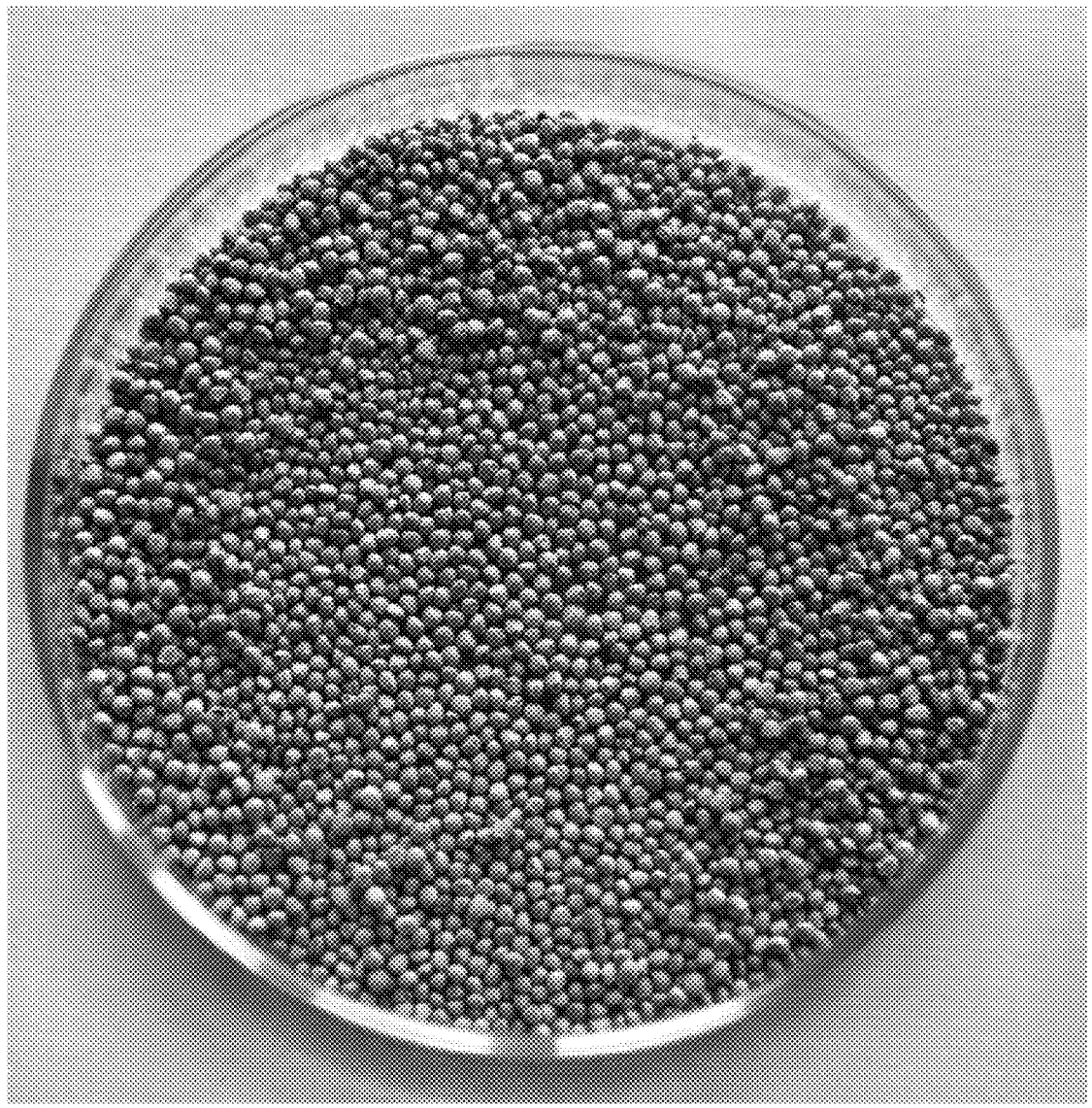
FIG. 3 shows the seeds of the plant CAP HEMA

FIG. 4 shows *Perilla* crop at the time of harvesting

```
                        SEQUENCE LISTING

<160> NUMBER OF SEQ ID NOS: 15

<210> SEQ ID NO 1
<211> LENGTH: 17
<212> TYPE: DNA
<213> ORGANISM: Artificial sequence
<220> FEATURE:
<223> OTHER INFORMATION: Synthetic primer sequence

<400> SEQUENCE: 1
gagagagaga gagagat                                              17

<210> SEQ ID NO 2
<211> LENGTH: 17
<212> TYPE: DNA
<213> ORGANISM: Artificial sequence
<220> FEATURE:
<223> OTHER INFORMATION: Synthetic primer sequence

<400> SEQUENCE: 2
cacacacaca cacacaa                                              17

<210> SEQ ID NO 3
<211> LENGTH: 17
<212> TYPE: DNA
<213> ORGANISM: Artificial sequence
<220> FEATURE:
<223> OTHER INFORMATION: Synthetic primer sequence

<400> SEQUENCE: 3
cacacacaca cacacag                                              17

<210> SEQ ID NO 4
<211> LENGTH: 18
<212> TYPE: DNA
<213> ORGANISM: Artificial sequence
<220> FEATURE:
<223> OTHER INFORMATION: Synthetic primer sequence

<400> SEQUENCE: 4
agagagagag agagagyt                                             18

<210> SEQ ID NO 5
<211> LENGTH: 17
<212> TYPE: DNA
<213> ORGANISM: Artificial sequence
<220> FEATURE:
<223> OTHER INFORMATION: Synthetic primer sequence

<400> SEQUENCE: 5
ctctctctct ctctctt                                              17

<210> SEQ ID NO 6
<211> LENGTH: 18
<212> TYPE: DNA
<213> ORGANISM: Artificial sequence
<220> FEATURE:
<223> OTHER INFORMATION: Synthetic primer sequence
```

<400> SEQUENCE: 6
ctctctctct ctctctta                                                    18

<210> SEQ ID NO 7
<211> LENGTH: 18
<212> TYPE: DNA
<213> ORGANISM: Artificial sequence
<220> FEATURE:
<223> OTHER INFORMATION: Synthetic primer sequence

<400> SEQUENCE: 7
agagagagag agagagyc                                                    18

<210> SEQ ID NO 8
<211> LENGTH: 18
<212> TYPE: DNA
<213> ORGANISM: Artificial sequence
<220> FEATURE:
<223> OTHER INFORMATION: Synthetic primer sequence

<400> SEQUENCE: 8
agagagagag agagagya                                                    18

<210> SEQ ID NO 9
<211> LENGTH: 17
<212> TYPE: DNA
<213> ORGANISM: Artificial sequence
<220> FEATURE:
<223> OTHER INFORMATION: Synthetic primer sequence

<400> SEQUENCE: 9
agagagagag agagagg                                                     17

<210> SEQ ID NO 10
<211> LENGTH: 18
<212> TYPE: DNA
<213> ORGANISM: Artificial sequence
<220> FEATURE:
<223> OTHER INFORMATION: Synthetic primer sequence

<400> SEQUENCE: 10
cacacacaca cacacarc                                                    18

<210> SEQ ID NO 11
<211> LENGTH: 18
<212> TYPE: DNA
<213> ORGANISM: Artificial sequence
<220> FEATURE:
<223> OTHER INFORMATION: Synthetic primer sequence

<400> SEQUENCE: 11
acacacacac acacacyt                                                    18

<210> SEQ ID NO 12
<211> LENGTH: 19
<212> TYPE: DNA
<213> ORGANISM: Artificial sequence
<220> FEATURE:
<223> OTHER INFORMATION: Synthetic primer sequence

<400> SEQUENCE: 12
acacacacac acacacacg                                                   19

<210> SEQ ID NO 13

```
<211> LENGTH: 18
<212> TYPE: DNA
<213> ORGANISM: Artificial sequence
<220> FEATURE:
<223> OTHER INFORMATION: Synthetic primer sequence

<400> SEQUENCE: 13
agagagagag agagagac                                                 18

<210> SEQ ID NO 14
<211> LENGTH: 20
<212> TYPE: DNA
<213> ORGANISM: Artificial sequence
<220> FEATURE:
<223> OTHER INFORMATION: Synthetic primer sequence

<400> SEQUENCE: 14
gagagagaga gagagagaat                                               20

<210> SEQ ID NO 15
<211> LENGTH: 18
<212> TYPE: DNA
<213> ORGANISM: Artificial sequence
<220> FEATURE:
<223> OTHER INFORMATION: Synthetic primer sequence

<400> SEQUENCE: 15
acacacacac acacacyg                                                 18
```

OMEGA-3 RICH HIGH YIELDING CULTIVAR OF *PERILLA FRUTESCENS* 'CAP HEMA'

REFERENCE TO AN ELECTRONIC SEQUENCE LISTING

The contents of the electronic sequence listing (revised_sequence_listing_ST25.txt Size:3230 bytes; and Date of Creation: Feb. 5, 2020) is herein incorporated by reference in its entirety.

FIELD OF INVENTION

Present invention relates to a new and distinct *Perilla frutescens* cultivar 'CAP HEMA', which is particularly well suited for high seed, fatty oil yield and rich in omega-3 fatty acid.

BACKGROUND OF THE INVENTION

Reference to any prior art in this specification is not, and should not be taken as, an acknowledgment or any form of suggestion that this prior art forms part of the common general knowledge in any country.

*Perilla* (*Perilla frutescens* L. Britton) is a cross-pollinating edible plant which belongs to family Lamiaceae that is frequently used as one of the most popular garnishes and food colorants in some Asian countries and as part of popular and traditional Chinese herbal medicines to East Asia and a traditional crop of China, Japan, Korea, Thailand, other Asian countries and USA.

Longvah and Deosthale (1998) have demonstrated that *Perilla* seed is a potential source of food, that is rich in fat and protein of good quality, which can be used in both human and animal nutrition. They also demonstrated that the potential of *Perilla* seed protein can be increased by dehulling the seeds and then cooking them. *Perilla* seed is particularly used in India (P. G. Peiretti, 2011) and in Korea where the seeds are consumed as flavoring and nutritional sources in combination with cereals or vegetables after roasting (Shin and Kim, 1994). *Perilla* seeds and oil are good source of α-linolenic acid (C18:3 n-3; ALA) and other aspects of their dietary value have been researched (Longvah and Deosthale, 1991). *Perilla* oil is widely used as a salad, oil dressing or cooking medium (Shin and Kim, 1994). In India, one species, *P. frutescens* generally occurs. In Asia, especially East Asia, two distinct varieties are known on the basis of their morphological characters and uses; *P. frutescens* (L.) Britton var. *frutescens*, an oil crop and *P. frutescens* (L.) Britton var. *crispa* (Thunb.) Deane, a vegetable and a Chinese medicine. Var. *frutescens* is cultivated and weedy type, larger in size and has larger, soft seeds, whereas ornamental type red leaved var. *crispa* is smaller, has more branching, and has smaller hard seeds. In Indian Himalaya, only the cultivated and weedy types of *Perilla* (var. *frutescens*) generally occur, while ornamental variety being occasionally grown in gardens only.

In North-East India, the fresh leaves are eaten as leafy vegetable, young shoots and flowering tops are boiled in the form of soups and consumed with boiled rice for flavouring and seed oil is used in cooking. In Uttarakhand Himalayan region, the seeds of *Perilla* are eaten raw and also used to prepare 'Chutney (Sauce)'.

Seeds of *Perilla* are potential source of food that is rich in fat and protein of good quality, which is used in both human and animal nutrition. *Perilla* seed is particularly used in India and in Korea where the seeds are consumed as flavoring and nutritional source in combination with cereals or vegetables after roasting. The seeds and fatty oil are good source of polyunsaturated fatty acids (PUFA) such as α-linolenic acid ($C_{18:3}$; omega-3) and linoleic acid ($C_{18:2}$; omega-6). The consumption of *Perilla* seed oil has also been reported to improve learning ability, retinal function, suppression of carcinogenesis, metastasis, thrombosis, allergies and has shown potential beneficial efforts to decrease the circulating levels of serum cholesterol and triglycerides without toxicity in a short term animal experiment. Omega-3 fatty acids are important for a number of bodily functions, including muscles activity, blood clotting, digestion, fertility, cell division and growth.

Keeping in mind the importance of *Perilla*, the need for developing better plant type having high seed yield combined with fatty oil yield with consistent of omega-3 and omega-6 fatty acids was felt and planned breeding and selection process was undertaken at the experimental farm of CAP, Dehradun (Uttarakhand), India to develop the cultivar 'CAP HEMA'.

OBJECTS OF THE INVENTION

The main object of the present invention is to develop a novel variety for high seeds and oil yielding genotype of *Perilla frutescens* plant.

Another object of the present invention is to develop a genotype of *Perilla frutescens* which is rich in omega-3 fatty acids in its natural form which is advantageous in that it has a nutrient richness, a simple preparation method and a good health care effect.

SUMMARY OF THE INVENTION

In an embodiment of the invention, a new and distinct cultivar of *Perilla* plant as herein described as *Perilla frutescens* cultivar 'CAP HEMA' having accession number NCIMB 42768, belonging to family Lamiaceae. A seed of *Perilla frutescens* are deposited at NCIMB, UK having accession number NCIMB 42768 and has grayed white (156D) color. The *Perilla frutescens* cultivar produces fatty oil yield of at least 8.4 ql per hectare. Further, the *Perilla frutescens* cultivar produces seed yield of 18.8 ql per hectare and has a height of at least 226.7 cm in a maximum of 161 days. The *Perilla frutescens* cultivar shows full flowering in the cultivar takes place in maximum 131 days after sowing. The *Perilla frutescens* cultivar has 58.8% omega-3 fatty acids (Linolenic).

In another embodiment of the present invention, a method for producing *Perilla frutescens* cultivar comprising: (a) collecting seeds of 12 germplasm; (b) sowing the seeds; (c) selecting the seeds from *Perilla frutescens* accessions based on morphological and fatty oil content from the sown population in step (b); (d) sowing the superior seed accessions from step (c); and (e) repeating the step (c) and (d) in initial evaluation trial (IET), bench scale trial (BST) and pilot scale trial (PST); a new and distinct cultivar of *Perilla frutescens* named as CAP HEMA is found.

The germplasm are selected from Anjanisain (Tehri), Chaukhutia (Almora), Dunda (Uttarkashi), Forti (Champawat), Magroli (Chakrata), Samalta (Kalsi), Tapovan (Chamoli), Gaudaguon (Uttarkashi), Takula (Almora), Dharchula (Pithoragarh), Okhalkanda (Nainital), Maldevta (Dehradun) of Uttarakhand Himalaya region.

BRIEF DESCRIPTION OF ACCOMPANYING DRAWING

FIG. 1 shows the plant of *Perilla frutescens* cultivar 'CAP HEMA';

FIG. 3 shows the seeds of the plant CAP HEMA;

FIG. 4 shows *Perilla* crop at the time of harvesting

DETAILED DESCRIPTION OF THE INVENTION

The present invention will now be described more fully hereinafter. This invention may, however, be embodied in many different forms and should not be construed as limited to the embodiments set forth herein. Rather, these embodiments are provided so that this disclosure will be thorough and complete, and will fully convey the scope of the invention to those skilled in the art.

Definitions

Plant: As used herein, the term "plant" includes reference to an immature or mature whole plant, including a plant from which seed, grain, or anthers have been/have not been removed. Seed or embryo that will produce the plant may also be considered being the plant.

Plant Height: Plant height is taken from the top of the soil to the top node of the plant and is measured in centimeters.

Plant Parts: As used herein, the term "plant parts" (or a *Perilla frutescens* plant, or a part thereof) includes but is not limited to protoplasts, leaves, stems, roots, root tips, anthers, pistils, seed, grain, embryo, pollen, ovules, cotyledon, hypocotyl, pod, flower, shoot, tissue, petiole, cells, meristematic cells, and the like.

*Perilla frutescens* are annual plants with square stems and serrated leaves. The leaves are arranged in opposite pairs, and the leaf colors range from green to dark green. The flowers are white and the seeds can be soft and hard, being white, grey, brown, and dark brown in color. *Perilla* varieties are cross-fertile and intra-specific hybridization occurs naturally. Some varieties are considered invasive.

*Perilla* has number of essential oils which are generally extracted from the leaves of *Perilla*. About 50% to about 60% of perillaldehyde is responsible for so much of the aroma and taste of *Perilla*. There are other terpenes such as limonene, caryophyllene and farnesene. There are other chemotypes such as perillaketone (PK), esholziaketone (EK), perillene (PL) and various phenylpropanoids such as myristicin, dillapiole and elemicin. Citral is a type rich in rosefuran. *Perilla* oil typically is obtained by pressing the seeds of *Perilla* that contain about 35% to about 45% oil. Typically, *Perilla* oil is a rich source of omega-3 fatty acid (alpha-linolenic acid). As a drying oil, it is similar to tung oil or linseed oil and is sometimes used in paint, varnish, linoleum, printing ink, lacquers and other protective water proof coatings.

In an embodiment of the present invention, half-sib progeny selection was used to improve populations of cross pollinating crops. A genetically variable population of heterozygo as individuals is either identified or created by intercrossing several different parents. The best plants are selected based on individual superiority, outstanding progeny, or excellent combining ability. The selected plants are sown in isolation for production of a new genotype/cultivar.

Figure 2A:
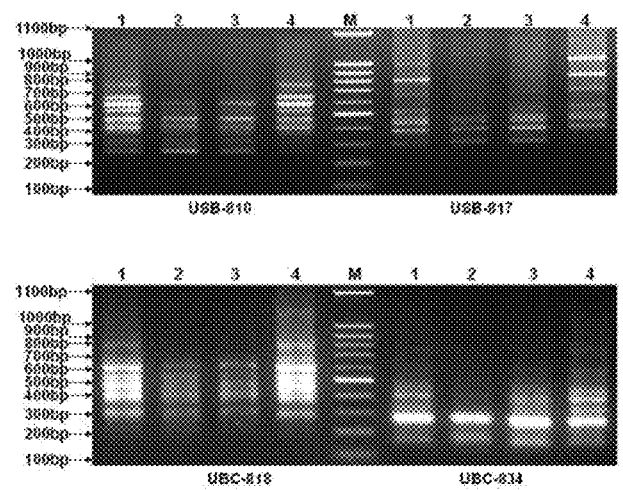
FIG. 2(*a-d*) shows DNA profile of the plant CAP HEMA.
Figure 2B:
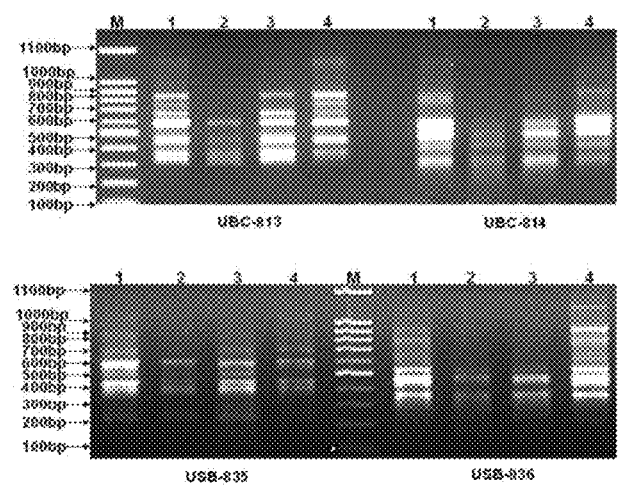
Figure 2C:
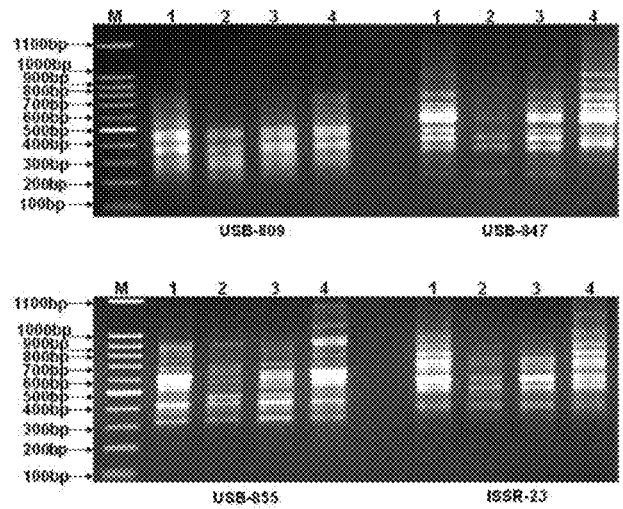
Figure 2D:
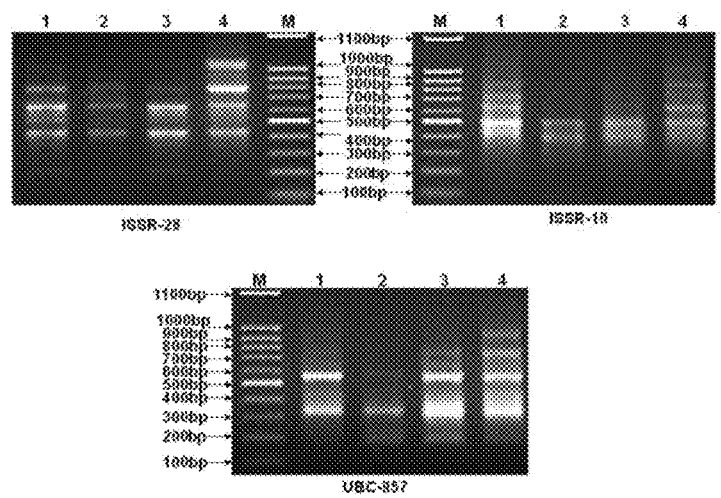

In an embodiment of the present invention provides FIG. 1 which shows the plant of *Perilla frutescens* cultivar 'CAP HEMA'. FIG. 2(*a-d*) which shows DNA profile of the plant CAP HEMA; FIG. 3 which shows the seeds of the plant CAP HEMA; and FIG. 4 which shows *Perilla* crop at the time of harvesting.

Examples

The present invention was carried out at Centre for Aromatic Plants (CAP) Dehradun, India under the genetic improvement of *Perilla frutescens*. The Germplasm (seeds) of *Perilla* were collected from different parts of Uttarakhand Himalayan region i.e. from Anjanisain (Tehri), Chaukhutia (Almora), Dunda (Uttarkashi), Forti (Champawat), Magroli (Chakrata), Samalta (Kalsi), Tapovan (Chamoli), Gaudaguon (Uttarkashi), Takula (Almora), Dharchula (Pithoragarh), Okhalkanda (Nainital), Maldevta (Dehradun).

The collected seeds of 12 accessions were sown in nursery and planted in progeny row trial in May, 2010. The sown nursery was transplanted in June, 2010 in the plot at a spacing of 60×30 cm. Out of 84 plants from each population, 50 plants were selected and seeds collected from individual plants were germinated in next season (May, 2011) and transplanted in the main field for evaluation of their performance in the month of June, 2011. The 7 best plant type out of 50 plants for seed yield and fatty oil and their contributing attributes were selected in each population for initial evaluation trial (IET) in May, 2012 and transplanted in June, 2012 under randomized block design. Observations were recorded from 25 randomly selected plants on morphological and fatty oil content from each population. After critical evaluation, 5 genotypes i.e. Ac.2-4-1, Ac.6-1-2, Ac.9-6-2, Ac.7-9-5 and Ac.10-8-3 were selected and seeds of these selected plants along with check (Local Bhangira Strain 'LBS-1') were sown in May, 2013 and transplanted in bench scale trial (BST) in randomized block design in June, 2013. The plot size was 4.2×3.6 m$^2$. Seedlings of each genotype planted at a spacing of 60×30 cm. Recommended agronomical practices has been adopted. Observations on plant height (cm), number of branches, number of spikes per plant, spike length (cm), seed yield (ql/ha), fatty oil content (%) and fatty oil yield (ql/ha) were recorded from randomly selected plants in each population and replication as illustrated in (Table 1 and 3).

Finally, out of 5 genotypes, 3 best promising genotypes Ac.2-4-1, Ac.6-1-2 and Ac.9-6-2 along with check LBS-1 were evaluated in 2014 in pilot scale trial (PST) as illustrated in Table 1. Collected seeds of each genotype along with check (LBS-1) sown in the month of May, 2014 in nursery plot and transplanted in June, 2014. The plot size was 4.2×3.6 m$^2$ and spacing was adopted 60×30 cm. In this trial, important yield and yield attributing components were recorded. Fatty oil content and oil quality components were analyzed.

On an average, the elite strain Ac.9-6-2 registered its superiority over all other selections including check LBS-1 for seed and fatty oil yield of better quality and other components per unit area. The elite strain was named as 'CAP HEMA'.

During screening and experimentation individual strains were maintained in seed plots with an isolation distance of 500 m$^2$ and seeds obtained from these seed plots were used in growing the plants for evaluation. During the evaluation trials, the plants were grown in isolation as mentioned are self pollinated and maintained the stability and purity as observed from the morphological and fatty oil profiles. The strain Ac.9-6-2 (subsequently named as 'CAP HEMA') consistently showed high seed yield and fatty oil content in BST and PST. In pilot scale trial (PST), the seed yield was 18.8 quintals per hectare. The total fatty oil yield was 8.4 quintals per hectare (table-1). All the yields (yield of seeds and oil) were higher than all other strains taken for comparison. The cultivar 'CAP HEMA' produced higher and better omega-3 in combination in the fatty oil compared to the check (table-2). Further, the physical characteristics of through restricting pollination within the population components maintained allelic balance within the population in nature of equilibrium. In the present invention the purity of the plant variety was maintained by growing the plant population with an isolation distance of 500 m from any other genotype of *Perilla frutescens*.

TABLE 1

Mean performance of promising strains in different yield trials for yield attributes, seed and fatty oil yield in Perilla (*Perilla frutescens*)

| | | Bench Scale Trial (RBD, Rep 4, plot size 15.12 m$^2$) | | | | | | Pilot Scale Trial (RBD, Rep 4, plot size 15.12 m$^2$) | | | | | |
|---|---|---|---|---|---|---|---|---|---|---|---|---|---|
| S. No. | Entries | Spikes per plant | Length of spike (cm) | Seed weight (g/plant) | Seed yield (ql/ha) | Fatty oil content (%) | Fatty oil yield (ql/ha) | Spikes per plant | Length of spike (cm) | Seed weight (g/plant) | Seed yield (ql/ha) | Fatty oil content (%) | Fatty oil yield (ql/ha) |
| 1 | Ac.2-4-1 | 145.0 | 12.7 | 53.9 | 15.0 | 43.7 | 6.6 | 149.3 | 13.7 | 54.7 | 15.2 | 42.3 | 6.4 |
| 2 | Ac.6-1-2 | 150.0 | 12.3 | 44.9 | 15.4 | 43.5 | 6.7 | 154.3 | 10.2 | 46.3 | 15.5 | 43.8 | 6.8 |
| 3 | Ac.9-6-2 | 157.0 | 13.4 | 54.4 | 18.3 | 44.2 | 8.1 | 158.7 | 16.7 | 55.3 | 18.8 | 44.5 | 8.4 |
| 4 | Ac.7-9-5 | 122.3 | 11.9 | 41.7 | 13.1 | 44.1 | 5.8 | — | — | — | — | — | — |
| 5 | Ac.10-8-3 | 149.7 | 10.5 | 42.2 | 15.5 | 44.0 | 6.8 | — | — | — | — | — | — |
| 6 | *LBS-1 | 75.0 | 9.7 | 31.4 | 9.4 | 42.9 | 4.0 | 92.6 | 9.1 | 32.4 | 9.5 | 43.6 | 4.2 |
| | SEm | 6.99 | 0.56 | 0.92 | 0.39 | 0.38 | 0.20 | 3.28 | 0.67 | 1.16 | 0.22 | 0.25 | 0.10 |
| | CD (5%) | 36.48 | 2.90 | 4.79 | 2.05 | 1.99 | 1.02 | 14.84 | 3.05 | 5.26 | 1.01 | 1.15 | 0.44 |

*Local Bhangira Strain-1 seeds of cultivar CAP HEMA that the seed color of cultivar CAP HEMA is grayed white (156D). The test weight (1000 seed weight) is 2.2 g, which more than LBS-1 i.e. maximum 1.6 g.

The Applicant has deposited seeds of the claimed *Perilla frutescens* cultivar named 'CAP HEMA' with the National Collection of Industrial Food and Marine Bacteria (NCIMB) Ltd., Ferguson Building, Craibstone Estate, Bucksburn, Aberdeen, AB21_9YA, Scotland, United Kingdom. The seeds are deposited under accession number NCIMB 42768. The date of the deposit was Jun. 13, 2017. The deposit was made under the provision of Budapest Treaty on the International Recognition of the deposit of Microorganisms for the purpose of Patent Procedure and Regulation thereunder (Budapest Treaty). This assures maintenance of a viable culture of the deposit for 30 years from the date of the deposit. The deposit will be made available by NCIMB under the terms of the Budapest Treaty, and subject to an agreement between NCIMB and the Centre for Aromatic Plants (CAP), India which assures permanent and unrestricted availability of the progeny of the culture of the deposit to the public.

This invention is also directed to methods for producing a *Perilla frutescens* by crossing a first parent *Perilla frutescens* plant with a second parent *Perilla frutescens* plant, wherein the first or second *Perilla frutescens* is the *Perilla frutescens* plant from cultivar 'CAP HEMA'. Further, both first and second parent *Perilla frutescens* plants may be from cultivar 'CAP HEMA'. Therefore, any methods using *Perilla frutescens* plant cultivar 'CAP HEMA' are part of this invention: selfing, backcrosses, hybrid breeding and crosses to populations. Any plants produced using *Perilla frutescens* cultivar 'CAP HEMA' as at least one parent is within the scope of this invention.

When the uniform plant population of *Perilla frutescens* cultivar 'CAP HEMA' is grown in isolation with minimum isolation distance of 500 m from other genotypes of *Perilla frutescens*, outcrossing from undesirable genotypes does not take place. Instead the population purity is being maintained Data recorded during BST and PST, is given after detailed statistical analysis using Analysis of Variance (ANOVA).

On an average, the elite strain Ac.9-6-2 registered its superiority over all other selections including check LBS-1 for seed and fatty oil yield of better quality and other components per unit area. The elite strain was named as 'CAP HEMA'.

TABLE 2

Fatty oil composition (%) of cultivar 'CAP HEMA' and check of *Perilla*

| S. No. | Fatty acids | CAP HEMA | Check (LBS-1) |
|---|---|---|---|
| 1 | $C_{14:0}$ Myristic | 0.35 | — |
| 2 | $C_{16:0}$ Palmitic | 6.78 | 10.9 |
| 3 | $C_{18:0}$ Stearic | 1.49 | 2.8 |
| 4 | $C_{18:1}$ Oleic | 14.55 | 14.3 |
| 5 | $C_{18:2}$ Linoleic (Omega-6) | 17.76 | 18.5 |
| 6 | $C_{18:3}$ Linolenic (Omega-3) | 58.80 | 51.4 |
| | Ratio (Linolenic:Linoleic) | 3.3:1 | 2.8:1 |

TABLE 3

Comparison of character of cultivar 'CAP HEMA' with the check (LBS-1)

| Attributes | CAP HEMA | Check (LBS-1) |
|---|---|---|
| Plant height (cm) | 226.7 | 155.6 |
| No. of branches per plant | 24.8 | 15.9 |
| Leaf length (cm) | 10.5 | 7.9 |
| Leaf width (cm) | 8.1 | 5.4 |
| Days taken to full flowering | 120-131 | 123-128 |
| Days taken to physiological maturity | 156-161 | 155-165 |
| Seed yield (ql/ha) | 18.8 | 9.5 |
| Test weight (g) | 2.2 | 1.6 |
| Fatty oil content (%) | 44.5 | 43.6 |
| Fatty oil yield (ql/ha) | 8.4 | 4.2 |

TABLE 3-continued

Comparison of character of cultivar 'CAP HEMA' with the check (LBS-1)

| Attributes | CAP HEMA | Check (LBS-1) |
|---|---|---|
| Omega-3 (%) | 58.8 | 51.4 |
| Omega-6 (%) | 17.76 | 18.5 |

Table 3 compares the characters of *Perilla frutescens* cultivar CAP HEMA with Local Bhangira Strain-1 (LBS-1). This table shows that improved cultivar has shown superiority in various attributes. The performance of LBS-1 was also checked during IET, BST and PST trials.

DNA Fingerprinting of Cultivar CAP HEMA

DNA Extraction

Nearly 30 seeds of cultivar CAP HEMA were grown in the germination paper and were harvested in bulk, placed in a sterilized mortar and frozen by adding liquid nitrogen and crushed vigorously with a pestle to a fine powder, care being taken to prevent thawing of the material. To prevent the powder from thawing, depending upon the necessity, little more liquid nitrogen was added while grinding. The ground material was immediately transferred to an autoclaved 50 ml centrifuge tube with 20 ml CTAB buffer maintained at 60° C. in a water bath. Vortexing was done for uniform mixing. The mixture was incubated at 60° C. for one hour in a water bath and mixed intermittently. Following incubation, an equal volume of chloroform and iso-amyl alcohol (24:1) was added to the tubes. The contents were mixed by gentle swirling for 2-5 minutes, following which the tubes were centrifuged at 13000 rpm for 15 minutes at 25° C. The aqueous phase was transferred to fresh tube, to which equal amount of iso-propanol was added and the contents were mixed by gentle inversions. DNA was allowed to settle down for 20 minutes and was spooled out into a 1 ml eppendorf tube. The pellet was washed twice with 70% ethanol and dried under vacuum. Finally, the pellet of DNA was dissolved in 200 µl of TE buffer (10:1) and stored at −20° C.

DNA Purification

The DNA was taken out from the deep freezer (−20° C.) and kept at ambient temperature for one hour. DNA was dissolved by keeping in a water bath maintained at 60° C. for 10-15 minutes. About 2.5 µl of RNase (1-mg/ml) was added and samples were incubated at 37° C. for one hour. An equal amount of phenol, chloroform and isoamyl alcohol (25:24:1) was added to the eppendorf tube and mixed by gently swirling for 5 minutes. The tubes were spun at 13,000 rpm for 15 minutes at 25° C. The aqueous phase was transferred to another eppendorf tube and washed with chloroform: isoamyl alcohol (24:1). Then DNA was precipitated by adding 1/10th volume of 3M sodium acetate and 2.5 times of the total volume chilled ethanol. Mixture was centrifuged at 13,000 rpm for 15 minutes. The liquid was drained away and salts were removed by two washings with 70% ethanol. The DNA pellet was dried in a lyophillizer and was dissolved in TE (10:1) at room temperature and stored at −20° C.

DNA Quantification

DNA Quantification was done using a Hoefer DyNA Quant 200 Flourometer. The concentration of unknown samples was estimated by adding 2 µl of DNA sample of unknown concentrations to 2 ml of assay buffer. A part of the DNA sample was diluted with appropriate amount of TE buffer to yield a working concentration of 10 ng/µl and stored at 4° C. An equal volume of diluted DNA from 10 individual plants of a particular sample was made into a bulk sample.

ISSR Analysis

ISSR analysis was carried out using 15 primers as listed in Table 4. PCR amplification was carried out with 50 ng of genomic DNA, 2.5 mM $MgCl_2$, 1 U Taq DNA polymerase. 1×PCR buffer (all reagents from M/S Sigma), 0.5 µM of primer and 0.2 mM of dNTP mix. The volume was made to 25 µl with sterile distilled water. PCR tubes containing the above components were capped and given a pulse spin to allow proper mixing of the reaction mixture. PCR was carried out in PTC 200 (M/S MJ Research) thermocycler. Thermo-cycling conditions were as follows:

Initial denaturation at 95° C. for 5 minutes.

Forty cycles of denaturation at 94° C. for 1 minute, annealing at 50° C. for 1 minute and primer extension at 72° C. for 1 minute.

Final extension step at 72° C. for 8 minutes.

Stored at 4° C. till removing from PCR machine.

Gel Electrophoresis

After completion of PCR amplification, 2.5 µl of loading dye (6×) was added to each PCR tube. Samples were loaded in 1.5% agarose gel and electrophoresed at 100V for 2 hours. The gels were stained with ethidium bromide. The resolved amplification products were visualized by illumination under UV light in a gel documentation system.

The banding pattern for the provided one sample using 15 ISSR primers is shown in FIG. 2(*a-d*) and the allele sizes are provided in Table 4.

Primers USB810, USB817, USB836, USB847, USB855, USB857, ISSR28 and ISSR10 produced markers specific to the provided sample (cultivar CAP HEMA) as compared to the control samples used in the analysis.

TABLE 4

Allele size observed in *Perilla frutescens* cultivar CAP HEMA sample

| PRIMER | SIZE | Control 1 | Control 2 | Control 3 | Sample (CAP HEMA) |
|---|---|---|---|---|---|
| USB-810 | 780 bp | 1 | 0 | 0 | 1 |
|  | 650 bp | 1 | 0 | 0 | 1 |
|  | 590 bp | 1 | 1 | 1 | 1 |
|  | 540 bp | 1 | 0 | 0 | 1 |
|  | 480 bp | 1 | 1 | 1 | 1 |
|  | 420 bp | 1 | 1 | 1 | 1 |
|  | 260 bp | 1 | 1 | 1 | 0 |
| USB-817 | 1000 bp | 0 | 0 | 0 | 1 |
|  | 800 bp | 1 | 0 | 0 | 1 |
|  | 680 bp | 0 | 0 | 0 | 1 |
|  | 520 bp | 1 | 0 | 0 | 1 |
|  | 430 bp | 1 | 1 | 1 | 1 |
|  | 425 bp | 0 | 0 | 1 | 0 |
|  | 380 bp | 1 | 1 | 1 | 0 |
|  | 300 bp | 1 | 1 | 1 | 0 |
| UBC-818 | 800 bp | 1 | 0 | 0 | 1 |
|  | 630 bp | 1 | 1 | 1 | 0 |
|  | 600 bp | 0 | 0 | 0 | 1 |
|  | 550 bp | 1 | 1 | 1 | 0 |
|  | 500 bp | 0 | 0 | 0 | 1 |
|  | 450 bp | 1 | 0 | 1 | 1 |
|  | 400 bp | 1 | 1 | 1 | 0 |
|  | 380 bp | 0 | 0 | 0 | 1 |
|  | 300 bp | 1 | 1 | 1 | 0 |
|  | 280 bp | 0 | 0 | 0 | 1 |
| UBC-834 | 400 bp | 1 | 0 | 0 | 1 |
|  | 380 bp | 0 | 0 | 1 | 1 |
|  | 300 bp | 0 | 0 | 0 | 1 |
|  | 280 bp | 1 | 1 | 0 | 0 |

TABLE 4-continued

Allele size observed in *Perilla frutescens* cultivar CAP HEMA sample

| PRIMER | SIZE | Control 1 | Control 2 | Control 3 | Sample (CAP HEMA) |
|---|---|---|---|---|---|
|  | 250 bp | 0 | 0 | 1 | 1 |
|  | 180 bp | 1 | 1 | 0 | 0 |
|  | 150 bp | 0 | 0 | 1 | 0 |
| UBC-813 | 850 bp | 1 | 0 | 1 |  |
|  | 800 bp | 0 | 0 | 0 | 1 |
|  | 750 bp | 1 | 0 | 0 | 1 |
|  | 650 bp | 1 |  | 1 | 1 |
|  | 550 bp | 1 | 1 | 1 | 1 |
|  | 450 bp | 1 | 0 | 1 | 1 |
|  | 360 bp | 1 | 1 | 1 | 1 |
|  | 340 bp | 1 | 1 | 1 | 0 |
| UBC-814 | 850 bp | 1 | 0 | 0 | 1 |
|  | 800 bp | 1 | 0 | 0 | 0 |
|  | 550 bp | 1 | 0 | 1 | 1 |
|  | 450 bp | 1 | 0 | 1 | 1 |
|  | 380 bp | 1 | 1 | 1 | 1 |
|  | 300 bp | 1 | 1 | 1 | 1 |
| USB-835 | 620 bp | 0 | 1 | 0 | 0 |
|  | 600 bp | 1 | 0 | 1 | 1 |
|  | 500 bp | 1 | 0 | 1 | 0 |
|  | 450 bp | 1 | 1 | 1 | 1 |
|  | 400 bp | 0 | 1 | 1 | 1 |
| USB-836 | 1250 bp | 0 | 0 | 0 | 1 |
|  | 900 bp | 0 | 0 | 0 | 1 |
|  | 800 bp | 0 | 0 | 0 | 1 |
|  | 520 bp | 1 | 0 | 0 | 1 |
|  | 450 bp | 1 | 1 | 1 | 1 |
|  | 370 bp | 1 | 1 | 1 | 1 |
| USB-809 | 510 bp | 1 | 0 | 0 | 0 |
|  | 480 bp | 1 | 1 | 1 | 1 |
|  | 440 bp | 1 | 1 | 1 | 1 |
|  | 350 bp | 1 | 1 | 1 | 1 |
| USB-847 | 950 bp | 0 | 0 | 0 | 1 |
|  | 850 bp | 0 | 0 | 0 | 1 |
|  | 780 bp | 1 | 0 | 0 | 1 |
|  | 740 bp | 0 | 0 | 0 | 1 |
|  | 680 bp | 1 | 0 | 1 | 1 |
|  | 550 bp | 1 | 0 | 1 | 1 |
|  | 480 bp | 1 | 0 | 1 | 1 |
|  | 400 bp | 1 | 1 | 1 | 1 |
|  | 390 bp | 0 | 0 | 0 | 1 |
|  | 370 bp | 1 | 1 | 1 | 0 |
| USB-855 | 1400 bp | 0 | 0 | 0 | 1 |
|  | 1200 bp | 0 | 0 | 0 | 1 |
|  | 900 bp | 0 | 0 | 0 | 1 |
|  | 880 bp | 1 | 1 | 0 | 1 |
|  | 680 bp | 1 | 0 | 1 | 1 |
|  | 650 bp | 0 | 0 | 1 | 1 |
|  | 620 bp | 1 | 0 | 1 | 0 |
|  | 450 bp | 0 | 1 | 1 | 0 |
|  | 420 bp | 1 | 1 | 1 | 1 |
|  | 320 bp | 1 | 1 | 1 | 1 |
| ISSR-23 | 800 bp | 0 | 0 | 0 | 1 |
|  | 740 bp | 1 | 0 | 0 | 1 |
|  | 680 bp | 1 | 0 | 1 | 1 |
|  | 660 bp | 1 | 0 | 0 | 1 |
|  | 550 bp | 1 | 0 | 1 | 1 |
|  | 520 bp | 0 | 0 | 0 | 1 |
|  | 480 bp | 1 | 1 | 1 | 1 |
|  | 360 bp | 1 | 1 | 1 | 0 |
| ISSR-28 | 1200 bp | 0 | 0 | 0 | 1 |
|  | 800 bp | 1 | 1 | 0 | 1 |
|  | 650 bp | 1 | 1 | 1 | 1 |
|  | 450 bo | 1 | 1 | 1 | 1 |
| ISSR-10 | 850 bp | 0 | 0 | 0 | 1 |
|  | 600 bp | 0 | 0 | 0 | 1 |
|  | 500 bp | 0 | 1 | 1 | 1 |
|  | 490 bp | 1 | 0 | 0 | 0 |
|  | 450 bp | 1 | 0 | 0 | 0 |
|  | 400 bp | 0 | 1 | 1 | 0 |
| UBC-857 | 950 bo | 0 | 0 | 0 | 1 |
|  | 750 bp | 0 | 0 | 0 | 1 |
|  | 550 bp | 1 |  | 1 | 1 |
|  | 340 bp | 1 | 1 | 1 | 1 |

Primers Sequences

| PRIMER | SEQ ID NO: | SIZE |
|---|---|---|
| USB-810 | SEQ ID NO: 1 | GAGAGAGAGAGAGAGAT |
| USB-817 | SEQ ID NO: 2 | CACACACACACACACAA |
| UBC-818 | SEQ ID NO: 3 | CACACACACACACACAG |
| UBC-834 | SEQ ID NO: 4 | AGAGAGAGAGAGAGAGYT |
| UBC-813 | SEQ ID NO: 5 | CTCTCTCTCTCTCTCTT |
| UBC-814 | SEQ ID NO: 6 | CTCTCTCTCTCTCTCTTA |
| USB-835 | SEQ ID NO: 7 | AGAGAGAGAGAGAGAGYC |
| USB-836 | SEQ ID NO: 8 | AGAGAGAGAGAGAGAGYA |
| USB-809 | SEQ ID NO: 9 | AGAGAGAGAGAGAGAGG |
| USB-847 | SEQ ID NO: 10 | CACACACACACACACARC |
| USB-855 | SEQ ID NO: 11 | ACACACACACACACACYT |
| ISSR-23 | SEQ ID NO: 12 | ACACACACACACACACACG |
| ISSR-28 | SEQ ID NO: 13 | AGAGAGAGAGAGAGAGAC |
| ISSR-10 | SEQ ID NO: 14 | GAGAGAGAGAGAGAGAGAAT |
| UBC-857 | SEQ ID NO: 15 | ACACACACACACACACYG |

Taxonomic description of cultivar 'CAP HEMA' of *Perilla frutescens*
1. Genus: *Perilla*
2. Species: *frutescens*
3. Family: Lamiaceae
4. Common name: Bhangira in Uttarakhand (India)
5. Plant height: approximately 226.7 cm (at maturity)
6. Number of branches: approximately 24.8/plant
7. Growth habit: Erect
8. Leaf shape: Ovate
9. Leaf apex: Caudate
10. Leaf margin: Serrate
11. Leaf venation: Reticulate
12. Leaf length: 10.5 cm
13. Leaf width: 8.09 cm
14. Leaf color: Green (143C)
15. Leaf texture: Rough
16. Leaf Surface: Hairy
17. Stem: Square
18. Stem color: Yellow Green (144C)
19. Flower inflorescence: Spike
20. Flower color: Whitish
21. Length of spike: 16.67 cm
22. Number of spikes per plant: 158
23. Number of spikelets per spike: 49
24. Seed size: 1.82 mm
25. Seed shape: Obovate
26. Seed color: Grayed White (156D)
27. 1000-seed weight (g): 2.2
28. Seed germinability: 84-88%

The color codes are in accordance with the R.H.S. Colour Chart (Sixth edition), Royal Horticultural Society, 80 Vincent Square, London, SW1P 2PE, 2015.

The foregoing invention has been described in some detail by way of illustration and example for purposes of clarity and understanding. However, it should be appreciated by those having ordinary skill in the art that certain changes and modifications such as single gene modifications and mutations, somaclonal variants, variant individuals selected from large populations of the plants of the instant inbred and the like may be practiced within the scope of the invention, as limited only by the scope of the appended claims, without departing from the true concept, spirit, and scope of the invention.

It is understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A new and distinct *Perilla frutescens* cultivar 'CAP HEMA' representative seeds of which are deposited at NCIMB, UK under accession number NCIMB 42768.

2. The *Perilla frutescens* cultivar of claim 1, wherein the cultivar produces fatty oil yield of at least 8.4 ql per hectare.

3. The *Perilla frutescens* cultivar of claim 1, wherein the cultivar produces a seed yield of 18.8 ql per hectare.

4. The *Perilla frutescens* cultivar of claim 1, wherein the cultivar has a height of at least 226.7 cm in a maximum of 161 days.

5. The *Perilla frutescens* cultivar of claim 1, wherein full flowering in the cultivar takes place in maximum 131 days after sowing.

6. The *Perilla frutescens* cultivar of claim 1, wherein the cultivar has 58.8% omega-3 fatty acids.

7. The *Perilla frutescens* cultivar of claim 1, wherein the seed has a grayed white (156D) color.

8. A method for producing the *Perilla frutescens* cultivar of claim 1, comprising:
   a) collecting germplasm of 12 different *Perilla frutescens* accessions in the form of seeds;
   b) sowing the seeds;
   c) selecting superior seeds based on morphological and fatty oil content from the sown population in step (b);
   d) sowing the superior seeds from step (c); and
   e) repeating the step (c) and (d) in initial evaluation trial (JET), bench scale trial (BST) and pilot scale trial (PST); wherein the method produces a new and distinct cultivar of *Perilla frutescens* cultivar 'CAP HEMA' (NCIMB accession number 42768) wherein the different germplasm/seeds of *Perilla frutescens* accessions are collected from the different geographical places/locations selected from Anjanisain (Tehri), Chaukhutia (Almora), Dunda (Uttarkashi), Forti (Champawat), Magroli (Chakrata), Samalta (Kalsi), Tapovan (Chamoli), Gaudaguon (Uttarkashi), Takula (Almora), Dharchula (Pithoragarh), Okhalkanda (Nainital), and Maldevta (Dehradun).

* * * * *